United States Patent [19]
Bell

[11] Patent Number: 6,021,253
[45] Date of Patent: Feb. 1, 2000

[54] HEATING PROBE

[75] Inventor: Michael L. Bell, Fullerton, Calif.

[73] Assignee: Beckman Coulter, Inc., Fullerton, Calif.

[21] Appl. No.: 08/874,117

[22] Filed: Jun. 12, 1997

[51] Int. Cl.[7] .............................. G01N 1/14; G01N 1/44
[52] U.S. Cl. .................. 392/338; 73/863.11; 73/864.21; 73/864.85
[58] Field of Search .................................. 392/312, 338; 73/863.11, 863.12, 864.21, 864.81, 864.85, 864.86, 864.87

[56] References Cited

U.S. PATENT DOCUMENTS

| | | |
|---|---|---|
| 3,463,012 | 8/1969 | McKinney et al. . |
| 3,917,454 | 11/1975 | Clark ..................................... 73/863.11 |
| 4,408,117 | 10/1983 | Yurkanin .................................. 392/441 |
| 4,788,150 | 11/1988 | Nelson et al. ............................. 436/45 |
| 5,039,322 | 8/1991 | Hölzl .................................... 73/863.24 |
| 5,178,019 | 1/1993 | Keiter ................................... 73/863.11 |
| 5,236,666 | 8/1993 | Hulette et al. ............................ 422/65 |
| 5,287,758 | 2/1994 | Geiss et al. ........................... 73/864.01 |
| 5,380,091 | 1/1995 | Buchanan ........................... 73/61.76 X |
| 5,814,721 | 9/1998 | Mills ..................................... 73/53.01 |

OTHER PUBLICATIONS

Harvey Mudd College Engineering Clinic, Final Report to Beckman Instruments: Temperature Controlled Probe, May 1993, (abstract 1st page only, pp. CC–V, pp. 1–18, 5 pages of Appendices).

*Primary Examiner*—Thomas P. Noland
*Attorney, Agent, or Firm*—William H. May; Margaret A. Kivinski; Steven G. Roeder

[57] ABSTRACT

A probe for heating a reagent and/or a test specimen from a storage temperature to an analysis temperature is provided herein. The probe is particularly useful with or as part of a clinical analyzer. The probe includes an electrically conductive, tubular inner structure and an electrically conductive, tubular outer structure which substantially encompasses the inner structure. An insulator is positioned between the inner structure and the outer structure which electrically separates the inner structure from the outer structure. Further, an interconnector electrically connects the inner structure to the outer structure. An electrical supply supplies current to the probe which flows through the inner structure and the outer structure to heat the reagent or the test specimen.

31 Claims, 2 Drawing Sheets

HEATING PROBE

FIELD OF THE INVENTION

The present invention relates to a probe for transferring a fluid between containers. The probe provided herein is particularly useful with an automated clinical analyzer for rapidly heating reagents from a refrigerated storage temperature to an analysis temperature.

BACKGROUND OF THE INVENTION

Automated clinical analyzers are commonly used to analyze a test specimen, i.e., serum or plasma, to determine the health of a patient and what measures are necessary to restore health to the patient. Clinical analyzers are presently able to quickly and accurately perform such functions as drug discovery, specific protein blood analysis and cancer detection on the test specimen. These clinical analyzers commonly utilize a plurality of reaction containers which are sequentially subjected to a variety of tests during a machine cycle of the clinical analyzer. During the machine cycle, a variety of fluids, including the test specimens and a number of reagents, are selectively dispensed into the reaction containers with a probe to perform the analysis.

Prior to analysis, the reagents are typically stored at a relatively cool storage temperature, i.e., approximately Four Degrees Celsius (4° C.). This inhibits degradation of the reagents prior to analysis with the clinical analyzer. However, it is often desirable to perform the analysis with the reagents at a higher temperature, referred to herein as an analysis temperature. In many cases, the analysis temperature is approximately human body temperature, i.e., approximately Thirty-Seven Degrees Celsius (37° C.). Accordingly, it is often necessary to heat the reagents prior to analysis with the clinical analyzer.

Presently, with some clinical analyzers, the reagents are heated from the storage temperature to the analysis temperature in the reaction container of the clinical analyzer. However, this wastes machine time of the clinical analyzer and diminishes the number of test specimens which can be analyzed by the clinical analyzer.

Alternately, others have attempted to heat the reagents during transfer from storage with a heating probe. For example, one version of a heating probe utilizes a heating element which directly contacts the probe. However, poor heat transfer between the heating element, the probe, and the fluid typically results in relatively long heating times and poor responsiveness to temperature fluctuations. A variation of this type of heating probe relies on a large thermal mass to quickly heat the fluid. However, the large thermal mass is too wide to fit into most receptacles. Still another variation of this type of heating probe includes preheating the probe to a higher temperature to store sufficient energy to rapidly heat the fluid. However, this can cause thermal damage to the fluid initially entering the probe lumen.

Another version of a heating probe includes directly passing electrical current through a conductive probe. However, the conductive probes have not proved to be satisfactory. For example, in order to obtain a rapid temperature change, some conductive probes are excessively long and require a significant amount of wash fluid to subsequently clean the wetted length of the probe. Other conductive probes have a very thin wall which is subject to bending. Moreover, some of the conductive probes use a connection wire connected proximate a probe tip so that current runs substantially the entire length of the probe. The connection wire is difficult to clean and often leads to carryover between fluids.

In light of the above, it is an object of the present invention to provide a device and method which accurately and rapidly heats test specimens and/or reagents from storage temperature to analysis temperature. Another object of the present invention is to provide a device and method which heats test specimens and/or reagents without wasting machine time of a clinical analyzer, without interrupting the operation of the clinical analyzer, and without damaging the test specimens and/or reagents. Yet another object of the present invention is to provide a device for heating test specimens and reagents which is relatively easy to manufacture, operate, and clean. Still another object of the present invention is to provide a probe which is not excessively long, fits into most reaction containers, and uses current levels within the limits established by regulatory agencies.

SUMMARY

The present invention is directed to a probe for heating a fluid, i.e., a test specimen and/or a reagent which satisfies these objectives. The probe disclosed herein is particularly useful for simultaneously transferring a fluid from a first receptacle to a second receptacle while heating the fluid. The probe includes an inner structure defining a probe lumen, an outer structure, and an interconnector electrically connecting the inner structure to the outer structure. In use, electrical current from an electrical supply is supplied to the inner structure and the outer structure to heat the fluid.

Typically, the inner structure is a conductive tube which receives the fluid. Since the inner structure directly contacts the fluid, it is important to maximize the heating capabilities of the inner structure. Thus, the electrical resistance of the inner structure should be maximized. This can be accomplished by minimizing the cross-sectional area of the inner structure and making the inner structure of a material which has a relatively high electrical resistance.

Typically, the outer structure is also a conductive tube. The outer structure encompasses at least a portion of the inner structure and provides support to the inner structure. Further, the outer structure provides a return path for the electrical current to the electrical supply.

Since the outer structure provides support to the probe and the majority of heat is supplied by the inner structure, the outer structure preferably has a cross-sectional area which is greater than a cross-sectional area of the inner structure and may be made of a material having less electrical resistance than the inner structure. Typically, the outer structure has a cross-sectional area that is at least about one and one half (1.5) times and preferably about three (3) times more than the cross-sectional area of the inner structure.

Importantly, the present invention overcomes the deficiencies of prior art conductive probes by using a thin walled inner structure to supply the majority of heat to the fluid and a stronger outer structure to provide mechanical strength and a clean current return path to the probe.

The interconnector electrically connects the inner structure to the outer structure and allows current to pass from the inner structure to the outer structure. One example of a suitable interconnector comprises a weld which attaches a distal inner tip of the inner structure to a distal outer tip of the outer structure. Since the interconnector connects the distal inner tip to the distal outer tip, current passes substantially the entire length of the inner structure and the outer structure. Preferably, this weld also substantially, hermetically seals an interface formed between the distal inner tip and the distal outer tip so that the probe is relatively easy to clean.

Typically, an insulator is positioned between at least a portion of the inner structure and a portion of the outer structure. The insulator inhibits the flow of electrical current between the inner structure and the outer structure except at the interconnector. This causes current to flow substantially the entire length of the inner structure and the outer structure to maximize the heating capabilities of the probe.

Preferably, an air gap exists between the outer structure and the insulator to minimize heat transfer between the inner structure and the atmosphere.

The electrical supply includes a first connector and a second connector which are connected to the probe. A first conductor area of the inner structure is electrically connected to one of the connectors while a second conductor area of the outer structure is electrically connected to one of the connectors to form an electrical circuit. The actual direction of current flow is not important to the operation of the probe.

Importantly, the temperature of the probe can be controlled by controlling the amount of current flowing through the probe. Thus, a controller can be used to control the temperature of the probe by controlling the current flowing from the electrical supply through the inner structure and the outer structure.

The invention is also a method for heating a fluid retained in a first receptacle. The method includes drawing the fluid from the first receptacle into a probe lumen of a probe and heating the fluid. The probe includes an inner structure, an outer structure which encompasses at least a portion of the inner structure, and an interconnector electrically connecting the inner structure to the outer structure. The method includes passing current through at least a portion of the inner structure and a portion of the outer structure to heat the inner structure and the outer structure.

It is important to recognize that the probe provided herein quickly and accurately heats a fluid from storage temperature to analysis temperature without adversely affecting the integrity of the fluid. Therefore, the fluid can be presented to the clinical analyzer at the analysis temperature. Thus, the fluid does not have to be heated in the reaction container of the clinical analyzer. This saves machine time of the clinical analyzer.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
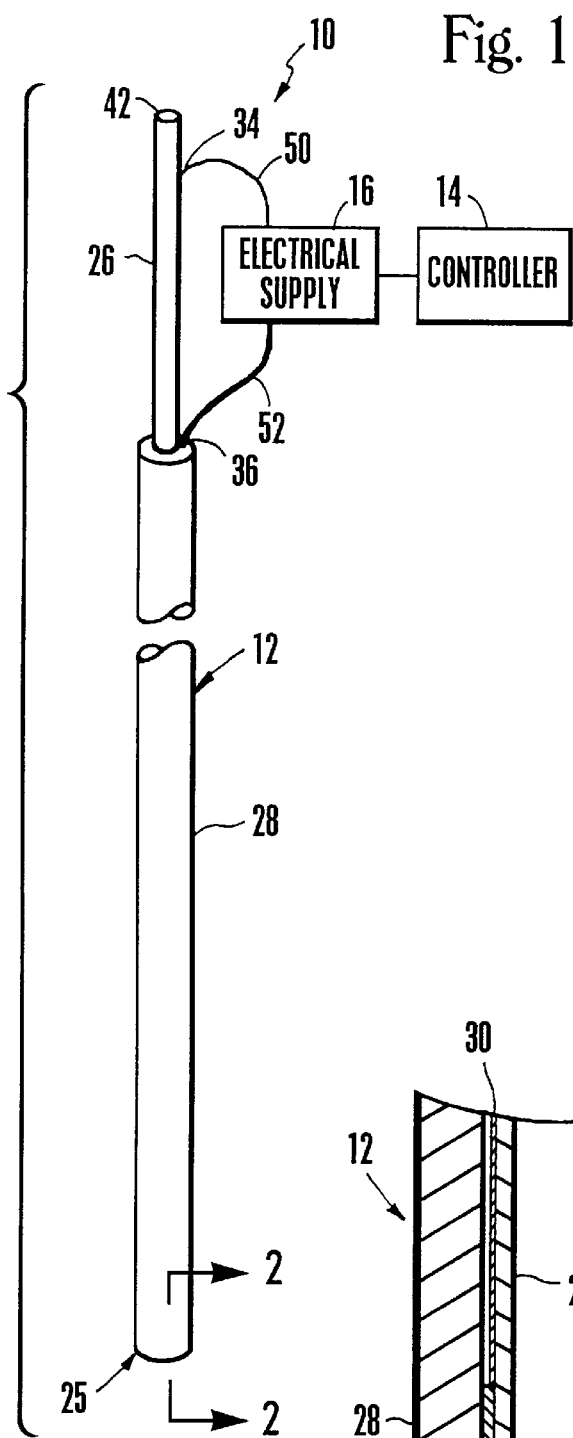
FIG. 1 is a perspective view of a probe assembly having features of the present invention.
Figure 3:
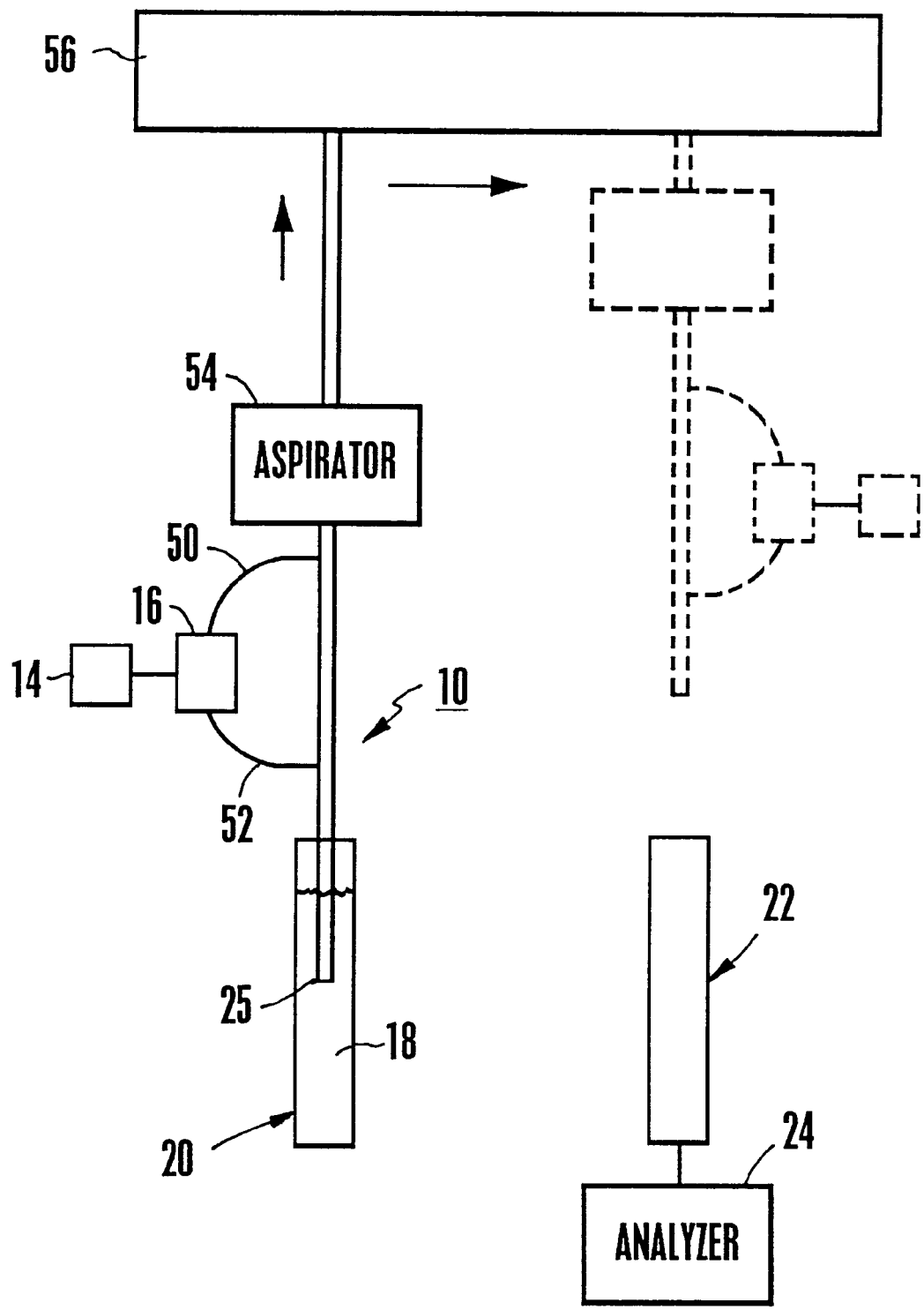
FIG. 3 is a simplified, side plan view of a probe assembly configured for operation in accordance with the present invention.

Referring initially to FIG. 1, a probe assembly 10 having features of the present invention includes a probe 12, an electrical supply 14 supplying current to the probe 12, and a controller 16 for controlling the temperature of the probe 12. As shown in FIG. 3, the probe assembly 10 can be used for simultaneously transferring a fluid 18 from a first receptacle 20 to a second receptacle 22 while heating the fluid 18 from a storage temperature to a higher analysis temperature.

The present invention is particularly useful for transferring fluids 18, such as test specimens, serum, plasma, whole blood samples, and/or reagents. However, it is anticipated that the probe 12 may be used to transfer other biological fluids, chemical fluids or reaction mixtures. For example, the probe 12 can be used to transfer urine or cerebral spinal fluid.

The storage temperature and the analysis temperature depend upon the fluid 18 and the type of tests which will be performed upon the fluid 18. For example, for reagents used for analyzing serum or plasma with a clinical analyzer 24 (see FIG. 3), the storage temperature is typically between about Zero Degrees Celsius to Ten Degrees Celsius (0° C.–10° C.) while the analysis temperature is between about Thirty Degrees Celsius to Forty-Five Degrees Celsius (30° C.–45° C.).

The probe 12 must be strong enough to not bend or deform during use. Accordingly, the design of the probe 12 depends upon the intended usage for the probe 12. For example, the probe 12 must be stronger if the probe 12 is used to remove and add fluids 18 from receptacles 20, 22 which are enclosed with a stopper (not shown).

Figure 2:
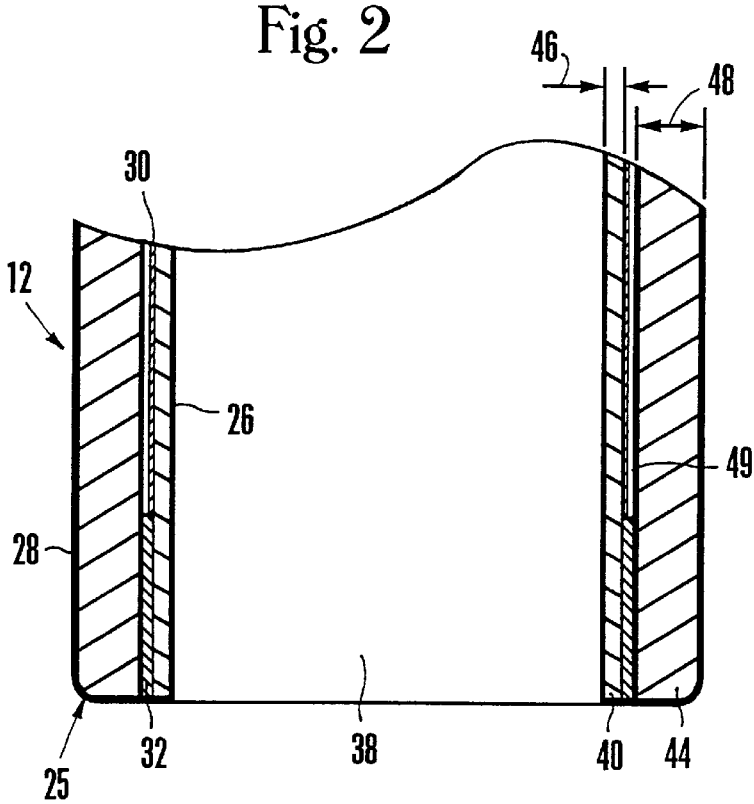
FIG. 2 is a cross-sectional view taken on line 2—2 in FIG. 1.

In the embodiment shown in FIGS. 1–3, the probe 12 includes a distal probe tip 25 which is annular shaped. Alternately, if the probe 12 is used to remove fluids 18 through a stopper (not shown), the distal probe tip 25 can be conical-shaped or wedge-shaped to facilitate piercing of the stopper.

Referring to FIG. 2, the probe 12 includes an inner structure 26, an outer structure 28, an insulator 30, and an interconnector 32. Basically, current from the electrical supply 14 passes through the inner structure 26 and the outer structure 28 to heat the fluid 18. Accordingly, the inner structure 26 includes an inner conductor area 34 and the outer structure 28 includes an outer conductor area 36 which are electrically connected to the electrical supply 14 by first and second connectors 50 and 52 respectively.

The inner structure 26 defines a probe lumen 38 for retaining the fluid 18. The dimensions of the probe lumen 38 are largely determined by the volume of fluid 18 required to be transferred. For example, a clinical analyzer 24 may require between about two hundred (200) microliters to four hundred (400) microliters of fluid 18 to perform the analysis. Thus, for this example, the probe lumen 38 should retain at least about four hundred (400) microliters of fluid.

In the embodiment shown in the Figures, the inner structure 26 is substantially tubular and includes a distal inner tip 40 and an opposed probe outlet 42. Also, in the embodiment shown in the Figures, the outer structure 28 is substantially tubular and includes a distal outer tip 44. The outer structure 28 encircles a portion of the inner structure 26 and provides strength and support to the probe 12. As shown in FIG. 2, the outer structure 28 can be substantially concentric with the inner structure 26.

At least a portion of the inner structure 26 and a portion of the outer structure 28 are made of a conductive material. Preferably, substantially the entire inner structure 26 and substantially the entire outer structure 28 are made of a conductive material to minimize heating time and minimize the required length of the probe 12.

Additionally, to minimize the required length of the probe 12, current should run through the entire length of the inner structure 26. The outer structure 28 provides a return electrical path for the electrical current supplied to the inner structure 26. This is accomplished by electrically connecting the distal inner tip 40 to the distal outer tip 44 with the interconnector 32. This eliminates the need for a connection wire (not shown) which is difficult to clean.

The length and thickness of the inner structure 26 and the outer structure 28 vary according to the materials utilized, the desired heating temperature, and the desired heating time of the fluid 18. Preferably, the inner structure 26 provides the majority of the heat to the fluid 18 since the inner structure 26 directly contacts the fluid 18 and more rapidly transfers heat to the fluid 18. Thinner walls have more electrical resistance and provide more heat for a given current. Similarly, a smaller cross-sectional area for a given current will provide more resistance. Thus, to maximize the heating capacity and minimize the fluid thermal response time, a cross-sectional area of the inner structure should be less than a cross-sectional area of the outer structure.

Preferably, the cross-sectional area of the outer structure is at least about one and one half (1.5) times greater than the cross-sectional area of the inner structure. More preferably, the cross-sectional area of the outer structure 48 is at least three (3) times as large as the cross-sectional area of the inner structure 46.

The proportion of total heat generated by the inner structure 26 may be further increased by utilizing a material which has a relatively high electrical resistance. In contrast, the heating capacity of the outer structure 28 can be decreased by utilizing a material having a relatively low electrical resistance. Preferably, the inner structure 26 and outer structure 28 are made of a material which resists corrosion.

Suitable materials for the probe 12 include Inconel 625 and Stainless Steel 304. Since Inconel 625 has a relatively high resistivity when compared to the Stainless Steel 304, the inner structure 26 can be made of the Inconel 625 while the outer structure 28 is made out of the Stainless Steel 304. With these materials the inner structure 26 would have more resistance and would provide more heat than the outer structure 28 which is exposed to the atmosphere and is less responsive to temperature fluctuations of the fluid 18.

A suitable probe 12 can include an inner structure 26 and an outer structure 28 which are formed from a length of hollow tubing. For example, the inner structure 26 can be made of 16 Gauge XXTW and the outer structure 28 can be made of 14 Gauge XTW. With this embodiment, the inner structure 26 has an inside diameter of about 0.060 inches, an outside diameter of about 0.065 inches, and a wall thickness 46 of about 0.0025 inches. Also with this embodiment, the outer structure 28 has an inside diameter of about 0.072 inches, an outside diameter of about 0.083 inches, and a wall thickness 48 of about 0.0055 inches.

For the embodiment described above, it is estimated that approximately eighty-five percent (85%) of the heat generated by the probe 12 will occur in the inner structure 26. This is desirable since the inner structure 26 is in intimate thermal contact with the fluid 18. Further, it is estimated that the probe 12 is capable of heating about four hundred (400) microliters of fluid from about Zero Degrees Celsius to Ten Degrees Celsius (0° C.–10° C.) to about Thirty Degrees Celsius to Forty Degrees Celsius (30° C.–40° C.) in at least about two (2) seconds.

Referring again to FIG. 2, the insulator 30 is positioned between at least a portion of the inner structure 26 and the outer structure 28, and inhibits the flow of electrical current therethrough. Preferably, the insulator 30 separates substantially the entire inner structure 26 and the entire outer structure 28, so that the electrical current flows substantially the entire length of the probe 12. This maximizes the heating capabilities of the probe 12.

The insulator 30 can be implemented in a number of alternate ways. For example, in the embodiment shown in FIG. 2, the insulator 30 is a piece of heat shrinkable polyester tubing which is shrunk around the inner structure 26. The required thickness of the insulator 30 depends upon the type of material utilized. For the polyester tubing described above, a thickness of between about 0.0005 inches and 0.002 inches is acceptable.

Alternately, the insulator 30 can be a coating having good electrical insulation properties which is applied to an outer surface of the inner structure 26. A suitable coating includes glass which is applied to the inner structure 26 with a vapor deposition process. This coating is available from MetoLine Industries of Corona, Calif.

Optimally, the insulator 30 is positioned between and protected by the inner structure 26 and the outer structure 28, and is not exposed to a corrosive environment.

Referring to FIG. 2, the probe 12 can include a gap 49 between the outer structure 28 and the inner structure 26. The gap 49 acts as a thermal barrier and minimizes the amount of heat which is transferred from the inner structure 26 to the outer structure 28. The gap 49, shown in the Figures, is approximately 0.003 inches. The gap 49 can be filled with air or another fluid. Alternately, the gap 49 could be a vacuum.

The interconnector 32 electrically connects the inner structure 26 to the outer structure 28 and allows current to flow from the inner structure 26 to the outer structure 28. Preferably, the interconnector 32 is positioned proximate the distal probe tip 25, so that current flows substantially the entire length of the inner structure 26. In the embodiment shown in FIG. 2, the interconnector 32 attaches the distal inner tip 40 to the distal outer tip 44 and substantially seals an interface formed between the distal inner tip 40 and the distal outer tip 44. Thus, the interconnector 32 provides a connection between the inner structure 26 and the outer structure 28 and there is no irregular surface to trap contaminants or disrupt wash fluid.

The design of the interconnector 32 depends upon the design of the probe 12 and the material utilized for the inner structure 26 and the outer structure 28. For an inner structure 26 made from Inconel 625 and an outer structure 28 made from Stainless Steel 304, the interconnector 32 can be an electron beam weld. Alternately, the interconnector 32 can be a material, such as bronze or silver which is soldered or brazed to the inner structure 26 and the outer structure 28.

The electrical supply 14 supplies current to the inner structure 26 and the outer structure 28. For the embodiment of the probe 12 described above, the electric supply 14 selectively supplies current at about eight (8) amps and a voltage of about eight (8) volts. Importantly, regulatory agencies may set the parameters for the maximum allowed current. Accordingly, it is important to design the probe assembly 10 around these regulations. For example, the electrical supply 14 could be limited to less than about thirty-six (36) volts.

Referring to FIG. 1, the electrical supply 14 includes a first connector 50 and a second connector 52. The first connector 50 is electrically connected to the inner conductor area 34 while the second connector 52 is electrically connected to the outer conductor area 36. Each of the connectors 50, 52 can be a wire or some other conductor which extends between the probe 12 and the controller 16.

One of the connectors 50, 52 is considered the positive terminal of the electrical supply 14 while the other connector 50, 52 is considered the negative terminal of the electrical supply 14. The actual direction of current flow is unimportant. However, it should be recognized that the same magnitude of current flows through the inner structure 26 and the outer structure 28.

The controller 16 controls and adjusts the temperature of the probe 12 so that the desired temperature of the fluid 18 in the probe 12 is achieved. The speed of this adjustment depends on the electrical supply 14, the electrical resistance of the probe 12, the rate of heat transfer between the probe 12 and the fluid 18, and the thermal mass of the probe 12 and the fluid 18. A fast response is desired to rapidly bring the fluid 18 to analysis temperature.

The controller 16 can be implemented in a number of alternate ways. For example, the controller 16 can control the current flowing from the electrical supply 14 through the inner structure 26 and the outer structure 28 to control temperature. Basically, the controller 16 determines the temperature of the probe 12 and adjusts current accordingly. If the controller 16 determines that the temperature of the probe 12 is too high, current through the probe 12 is reduced. Alternately, if the controller 16 determines that the temperature of the probe 12 is too low, current through the probe 12 is increased.

The controller 16 can determine the temperature of the probe 12 in a number of alternate ways. For example, the inner structure 26 and the outer structure 28 can be made from materials, such as Inconel 625 and Stainless Steel 304 which undergo reasonably measurable changes in resistance around the analysis temperature. The controller 16 can measure the amount of current flowing through the probe 12 and the amount of voltage supplied by the electrical supply 14 to determine the resistance of the probe 12. With the resistance of the probe 12, the controller 16 can determine the approximate temperature of the probe 12. Therefore, the controller 16 adjusts or regulates the current in response to the temperature of the probe 12 as calculated by the resistance of the inner structure 26 and the outer structure 28.

As shown in FIG. 3, an aspirator 54 is connected to the probe outlet 42. The aspirator 54 aspires the fluid 18 into the probe lumen 38 and subsequently expels the fluid 18 from the probe lumen 38. A suitable aspirator 54 is a motorized syringe sold under the trademark Accuprep, by Beckman Instruments, Inc. located in Fullerton, Calif.

Referring again to FIG. 3, the present invention can include a mover 56 which selectively allows the probe 12 to move relative to the first and second receptacles 20, 22. This allows the probe 12 to transfer the fluid 18 from the first receptacle 20 to the second receptacle 22. The mover 56 can be implemented in a number of alternate ways. For example, the mover 56 can be a robotic arm (not shown) which moves the probe 12 to the proper position in the first receptacle 20 or the second receptacle 22. Alternately, the mover 56 can be a device which moves the first and second receptacles 20, 22 relative to the probe 12.

Typically, the first receptacle 20 is a storage container for the fluid 18. Depending upon the particular embodiment, the second receptacle 22 can, for example, be a reaction container for a clinical analyzer 24, a tube for a sample splitter (not shown), a tube for a centrifuge (not shown), a tube for a sample separator (not shown), a waste reservoir, or any other fluid container.

A clinical analyzer 24 sold by the assignee of the present invention, Beckman Instruments, Inc. of Fullerton, Calif., under the trademark Synchron CX®7, can be utilized with the present invention.

A key advantage of the present invention is that it decreases the time required to produce results with a clinical analyzer 24 by delivering the fluid 18 to the clinical analyzer 24 at the analysis temperature.

Operation

An example of the operation of a probe 12 having features of the present invention can best be visualized with initial reference to FIG. 3. The operation begins with the probe 12 being washed with a wash solution (not shown). The probe 12 is easy to clean because the interconnector 32 between the inner structure 26 and the outer structure 28 forms an easy to clean interface. Thus, there is less chance of carry-over between fluids 18 and a more vigorous, time consuming wash is not necessary.

Subsequently, the mover 56 moves the probe 12, so that the probe 12 is positioned within the first receptacle 20. At this time, the first receptacle 20 contains the fluid 18, i.e., serum or reagent, at a lower storage temperature. Next, a portion of the fluid 18, in the first receptacle 20, is aspirated into the probe lumen 38 with the aspirator 54.

If the fluid 18 is at a lower storage temperature, the controller 16 directs current through the inner structure 26 and the outer structure 28. This causes these structures 26, 28 to heat the fluid 18 from the storage temperature to the analysis temperature. The heating of the fluid 18 can occur during movement of the probe 12 by the mover 56.

Next, the probe 12 is positioned in the second receptacle 22. After the controller 16 indicates that the fluid 18 is at the desired analysis temperature, the aspirator 54 expels the fluid 18 from the probe lumen 38. Subsequently, the process can be repeated with a different fluid 18 and/or another container (not shown).

With the unique design of the present invention, the inner structure 26 provides most of the heat to the fluid 18, while the outer structure 28 provides the required strength to the probe 12. Further, the interconnector 32 connects the inner structure 26 to the outer structure 28 proximate the distal probe tip 25 so that current can be supplied through the entire length of the probe 12 to minimize the required length of the probe 12. Importantly, this allows the probe 12 to deliver the fluid 18 to the clinical analyzer 24 at the desired analysis temperature. Therefore, machine time of the clinical analyzer 24 is not consumed waiting for the fluid 18 to reach the desired analysis temperature.

While the particular probe assembly 10 and probe 12, as herein shown and disclosed in detail, is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A probe for heating a fluid, using an electrical supply having a first connector and a second connector, the probe comprising:

an inner structure defining a probe lumen, at least a portion of the inner structure being electrically conductive and adapted for electrically connecting to one of the connectors;

an outer structure which encompasses at least a portion of the inner structure, at least a portion of the outer structure being electrically conductive and adapted for electrically connecting to one of the connectors, the outer structure having a wall thickness which is greater than a wall thickness of the inner structure; and an interconnector for electrically connecting the inner structure to the outer structure.

2. The probe of claim 1 further comprising an insulator positioned between substantially the entire inner structure and substantially the entire outer structure, the insulator substantially inhibiting the flow of electrical current therethrough.

3. The probe of claim 2 including a gap between a portion of one of the structures and the insulator.

4. The probe of claim 1 wherein the inner structure and the outer structure are substantially tubular and the outer structure has a cross-sectional area which is at least about one and one half times as large as a cross-sectional area of the inner structure.

5. The probe of claim 1 wherein the inner structure is made of a material having a higher electrical resistance than the outer structure.

6. The probe of claim 1 wherein the interconnector is a weld which extends between the inner structure and the outer structure.

7. A probe assembly comprising:
the probe of claim 1;
an electrical supply having a first connector and a second connector for supplying current to the probe; and
a controller for controlling the flow of current to the probe.

8. The probe assembly of claim 7 including a mover which moves the probe and enables a probe tip of the probe to be alternately positioned in a first receptacle and a second receptacle.

9. A clinical analyzer including a reaction container and the probe of claim 1, wherein the probe includes a probe tip which is sized and shaped to fit within the reaction container.

10. The probe of claim 1 wherein the probe is capable of heating about four hundred microliters of fluid about thirty degrees Celsius to forty degrees Celsius in at least about two seconds.

11. The probe of claim 1 including means for drawing the fluid from a first receptacle through a probe tip of the probe into the probe lumen of the inner structure, means for heating the fluid in the probe lumen by passing a current through at least a portion of the inner structure and a portion of the outer structure, and means for expelling the fluid from the probe lumen out the probe tip.

12. The probe of claim 11 wherein the means for expelling the fluid includes expelling the fluid from the probe lumen out the probe tip into a second receptacle.

13. The probe of claim 11 including means for controlling the flow of current through the inner structure and the outer structure.

14. The probe of claim 1 wherein the probe lumen is sized and shaped to retain between approximately two hundred microliters and four hundred microliters of fluid.

15. The probe of claim 1 wherein the wall thickness of the outer structure is approximately two times greater that the wall thickness of the inner structure.

16. The probe of claim 1 including a controller which adjusts the current in the inner structure and the outer structure in response to the temperature of the probe as determined by a resistance of the inner structure and the outer structure.

17. A probe for selectively heating a fluid, using an electrical supply having a first connector and a second connector, the probe comprising:

an electrically conductive, tubular, inner structure having a probe lumen and a distal inner tip, the inner structure also including an inner conductor area for electrically connecting one of the connectors to the inner structure;

an electrically conductive, tubular, outer structure which substantially encircles a portion of the inner structure, the outer structure having a distal outer tip and an outer conductor area for electrically connecting one of the connectors to the outer structure;

an insulator positioned between substantially the entire inner structure and the outer structure, the insulator substantially inhibiting the flow of electrical current between the inner structure and the outer structure; and an interconnector electrically connecting the inner structure to the outer structure proximate the distal inner tip and the distal outer tip.

18. The probe of claim 17 including a gap between a portion of one of the structures and the insulator.

19. The probe of claim 17 wherein the outer structure has a cross-sectional area which is at least about one and one half times as large as a cross-sectional area of the inner structure and wherein the outer structure has a wall thickness which is greater than a wall thickness of the inner structure.

20. The probe of claim 17 wherein the interconnector comprises a weld which extends between the inner tube and the outer tube and attaches the distal inner tip to the distal outer tip and substantially seals an interface formed between the distal inner tip and the distal outer tip.

21. A probe assembly comprising:
the probe of claim 17;
an electrical supply having a positive connector and negative connector for supplying current to the probe; and
a controller for controlling the flow of current to the probe.

22. The probe assembly of claim 21 wherein the controller measures the amount of current flowing through the probe to determine the temperature of the probe.

23. A clinical analyzer including a reaction container and the probe of claim 21, wherein the probe includes a probe tip which is sized and shaped to fit within the reaction container.

24. A probe assembly for heating a fluid, using an electrical supply having a first connector and a second connector, the probe assembly comprising:

a probe including (i) an inner structure defining a probe lumen, at least a portion of the inner structure being electrically conductive and adapted for electrically connecting to one of the connectors; (ii) an outer structure which encompasses at least a portion of the inner structure, at least a portion of the outer structure being electrically conductive and adapted for electrically connecting to one of the connectors; and (iii) an interconnector for electrically connecting the inner structure to the outer structure; and an aspirator for drawing the fluid through a probe tip of the probe into the probe lumen and expelling the fluid from the probe lumen out the probe tip.

25. The probe assembly of claim 24 wherein the probe lumen is sized and shaped to retain between approximately two hundred microliters and four hundred microliters of fluid.

26. The probe assembly of claim 24 wherein a wall thickness of the outer structure is greater that a wall thickness of the inner structure.

27. The probe assembly of claim 24 including an insulator positioned between substantially the entire inner structure and substantially the entire outer structure, the insulator substantially inhibiting the flow of electrical current therethrough.

28. A probe assembly for heating a fluid and transferring the fluid from a first receptacle to a second receptacle, using an electrical supply having a first connector and a second connector, the probe assembly comprising:

a probe including (i) an inner structure defining a probe lumen, at least a portion of the inner structure being electrically conductive and adapted for electrically connecting to one of the connectors; (ii) an outer structure which encompasses at least a portion of the inner structure, at least a portion of the outer structure being electrically conductive and adapted for electrically connecting to one of the connectors; and (iii) an interconnector for electrically connecting the inner structure to the outer structure; and a mover adapted to selectively move a probe tip of the probe from the first receptacle to the second receptacle.

29. The probe assembly of claim 28 wherein the probe lumen is sized and shaped to retain between approximately two hundred microliters and four hundred microliters of fluid.

30. The probe assembly of claim 28 wherein a wall thickness of the outer structure is greater that a wall thickness of the inner structure.

31. The probe assembly of claim 28 including an insulator positioned between substantially the entire inner structure and substantially the entire outer structure, the insulator substantially inhibiting the flow of electrical current therethrough.

* * * * *